US009284577B2

United States Patent
Watanabe et al.

(10) Patent No.: US 9,284,577 B2
(45) Date of Patent: Mar. 15, 2016

(54) STRAIN CLASSIFIED UNDER BOTRYOCOCCUS BRAUNII

(75) Inventors: Makoto Watanabe, Ibaraki (JP); Kunimitsu Kaya, Ibaraki (JP); Takako Tanoi, Ibaraki (JP); Masanobu Kawachi, Ibaraki (JP); Makoto Shiho, Ibaraki (JP)

(73) Assignee: University of Tsukuba, Ibaraki (JP)

( * ) Notice: Subject to any disclaimer, the term of this patent is extended or adjusted under 35 U.S.C. 154(b) by 118 days.

(21) Appl. No.: 13/992,590

(22) PCT Filed: Dec. 9, 2011

(86) PCT No.: PCT/JP2011/078606
§ 371 (c)(1),
(2), (4) Date: Jun. 7, 2013

(87) PCT Pub. No.: WO2012/077804
PCT Pub. Date: Jun. 14, 2012

(65) Prior Publication Data
US 2013/0252304 A1 Sep. 26, 2013

(30) Foreign Application Priority Data
Dec. 9, 2010 (JP) .................................. 2010-275105

(51) Int. Cl.
C12P 5/02 (2006.01)
C12N 1/12 (2006.01)
C12P 5/00 (2006.01)
C12R 1/89 (2006.01)

(52) U.S. Cl.
CPC . *C12P 5/026* (2013.01); *C12N 1/12* (2013.01); *C12P 5/007* (2013.01); *C12R 1/89* (2013.01)

(58) Field of Classification Search
None
See application file for complete search history.

(56) References Cited

FOREIGN PATENT DOCUMENTS

JP H09173050 A 7/1997

OTHER PUBLICATIONS

Weiss et al., J. Biol. Chem. 285(42): 32458-32466 (Oct. 15, 2010).*
Yoshimura et al., Bioresource Technology 133: 232-239 (2013).*
Dayananda, C., et al., Presence of methyl branched fatty acids and saturated hydrocarbons in botryococcene producing strain of Botryococcus braunii, ACTA Physiologiae Plantarum. vol. 28, No. 3, 2006: 251-256.
Metzger, P. et al., "Botryococcus braunii: a rich source for hydrocarbons and related ether lipids," Appl. Microbiol. Biotechnol. (2005) 66: 486-496.
Okada, S., et al., Hydrocarbon Production by the Yayoi, a New Strain of the Green Microalga Botryococcus braunii, Applied Biochemistry and Biotechnology, vol. 67, 1997, pp. 79-87.
Weiss, T.L., et al., Raman Spectroscopy Analysis of Botryococcene Hydrocarbons from the Green Microalga Botrycoccus braunii, The Journal of Biological Chemistry, vol. 285, No. 42, pp. 32458-32466, Oct. 15, 2010.

* cited by examiner

*Primary Examiner* — Patricia A Leith
*Assistant Examiner* — Erin M Bowers
(74) *Attorney, Agent, or Firm* — Kenyon & Kenyon LLP

(57) ABSTRACT

Provision of a novel strain belonging to *Botryococcus braunii*, capable of growth under a wide range of culturing conditions, having a high produced hydrocarbon content, and having high purity of the target hydrocarbon.

13 Claims, 3 Drawing Sheets

STRAIN CLASSIFIED UNDER BOTRYOCOCCUS BRAUNII

TECHNICAL FIELD

The present invention relates to a novel strain belonging to *Botryococcus braunii*, capable of growth under a wide range of culturing conditions, having a high hydrocarbon content, and having high purity of the target hydrocarbon.

BACKGROUND ART

In recent years, development has been advancing in the field of technologies for atmospheric carbon dioxide reduction, as a countermeasure against global warming. Research on renewable energy continues to progress as well from the point of view of the sense of crisis regarding fossil fuel depletion. Implemented renewable energy sources include solar photovoltaic power generation and wind power generation, but the use of photosynthetic organisms that convert water and carbon dioxide to hydrocarbons by light energy is also attracting interest.

Algae are photosynthetic organisms of interest as energy resources, with particular focus being directed toward green algae and diatoms. Most green algae have 15-17% lipids in their constituent components, the lipids being roughly classified as neutral lipids (30%), glycolipids (37%), phospholipids (26%) and non-fatty acid lipids (7%).

In recent years, particular interest has been focusing on the oil-producing green algae, *Botryococcus braunii*. The main components of the lipids produced by *Botryococcus braunii* are hydrocarbons composed of carbon and hydrogen, and they are known to store hydrocarbons such as straight-chain alkenes and triterpenes both intracellularly and extracellularly.

*Botryococcus braunii* is classified into race-A, race-B and race-L based on the structural characteristics of the produced hydrocarbons. By definition, race-A is a group that produces hydrocarbons with an odd number of carbons between 25 and 31, straight-chain, and having 2 or 3 double bonds in the molecule, race-B is a group producing hydrocarbons with a triterpene structure represented by $C_nH_{2n-10}$ (n=30-37), and race-L is a group that produces hydrocarbons having a tetraterpene lycopadiene (lycopadiene) ($C_{40}H_{78}$) structure.

The hydrocarbon contents of *Botryococcus braunii* strains belonging to each of these groups may be found in previously published reports. Variations exist between the strains in race-A, but the contents have been reported to be in the range of 0.4-61.0% (hydrocarbon weight with respect to cell dry weight) (Non-patent literature 1). In race-B, hydrocarbon content is generally 30-40% of cell dry weight, but some strains have been reported to produce only about 9 Non-patent literature (Non-patent literature 2). In race-L, 0.1% has been reported for an Indian strain and 8.0% for a Thai strain (Non-patent literature 3), which are low values compared to race-B. The hydrocarbons are mixtures of various carbon chain lengths and/or structures.

These hydrocarbons can be utilized without treatment, as heavy oils for production of thermal energy, but they are preferably used after further processing, as homogeneous hydrocarbon compositions to serve as materials for obtaining homogeneous compounds. There has also been a need for a strain having a simple hydrocarbon synthetic pathway, as a model for physiological research toward application of *Botryococcus*.

In addition, while low-cost mass culturing methods have been established for realizing industrialization of *Botryococcus*, there has been a need for outdoor culturing using sunlight, in order to minimize costs. In this case, since light quantity is the major growth limiting factor, it is most efficient to carry out culturing in seasons and locations with high intensity of solar radiation, using pools with low water levels and thin bioreactors. When culturing is carried out by such methods, however, the water temperature increases, and therefore the existing *Botryococcus* strains whose optimum growth temperature is between 15° C. and 30° C. and cease growth at 35° C. or higher and above, cease to grow during periods of maximum intensity of solar radiation. In actual results, in Tsukuba city during July, 2006, with outdoor culturing in a reactor with a water level depth of 10 centimeters, the maximum water temperature reached 37° C. A strain with an optimum growth temperature at a high temperature of 35° C. or higher has therefore been desired.

CITATION LIST

Patent Literature

[Patent Literature 1] Japanese Unexamined Patent Publication HEI No. 9-9953

Non-Patent Literature

[Non-patent literature 1] Metzger, P., Berkaloff, C., Coute, A., Casadevall, E. (1985) Alkadiene- and botryococcene-producing races of wild strains of *Botryococcus braunii*. Phytochemistry 24, 2305-2312.

[Non-patent literature 2] Okada, S., Murakami, M., Yamaguchi, K. (1995) Hydrocarbon composition of newly isolated strains of green alga *Botryococcus braunii*. J. Appl. Phycol. 7, 555-559.

[Non-patent literature 3] Metzger, P., Pouet, Y., Summons, S. (1997) Chemotaxonomic evidence for similarity between *Botryococcus braunii* L race and *Botryococcus neglectus*. Phytochemistry 24, 2305-2312.

DISCLOSURE OF THE INVENTION

Problems to be Solved by the Invention

In light of the demand described above, it is an object of the present invention to provide a novel strain belonging to *Botryococcus braunii*, capable of growth under a wide range of culturing conditions, with high purity of produced hydrocarbons.

Means for Solving the Problems

The present inventors have harvested *Botryococcus braunii* from the natural environment, and have discovered a strain with which the aforementioned object can be achieved, among strains of a group with a large number of phylogenetically different subgroups, isolating it and thereupon completing this invention.

(1) The invention provides a strain belonging to *Botryococcus braunii* race-B, that produces hydrocarbons of the molecular formula $C_{34}H_{58}$ at 60% of cell dry weight or greater with respect to the total produced hydrocarbons.

(2) The invention further provides a strain belonging to *Botryococcus braunii* race-B according to (1), wherein the optimal culturing temperature is 30° C. or higher.

(3) The invention further provides the strain *Botryococcus braunii* tsukuba-1 (deposit number: FERM ABP-11441, depositary institution: National Institute of Advanced Industrial Science and Technology, International Patent Organism Depositary (IPOD)).

(4) The invention further provides a strain belonging to *Botryococcus braunii* race-B according to any one of (1) to (3), which produces a hydrocarbon having the molecular formula $C_{34}H_{58}$ and having the structure of the following formula (I).

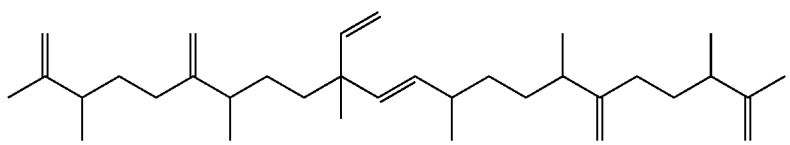

formula (I)

(5) The invention further provides a method for producing hydrocarbons from a strain belonging to *Botryococcus braunii* race-B according to any one of (1) to (4).

Effect of the Invention

The novel strain belonging to *Botryococcus braunii* race-B of the invention can produce hydrocarbon at high purity and is capable of growth under a wide range of culturing conditions.

Specifically, because the strain of *Botryococcus braunii* race-B according to the invention produces C34 hydrocarbons at high purity, it can be directly applied for heavy oils in ships and agricultural work vehicles, which can also be directly converted to light oil, naphtha, kerosene and gasoline by existing catalyst cracking systems. In addition, the strain of *Botryococcus braunii* race-B according to the invention can be cultured at a culturing temperature of about 10° C. to 45° C. and preferably about 15° C. to 40° C., and particularly it may be cultured at about 39° C. Since other algae belonging to the genus *Botryococcus* do not grow at 35° C. and higher, the strain of *Botryococcus braunii* race-B of the invention has the advantage that it can generally be selectively obtained by setting the culturing temperature higher than 35° C. It has the additional advantage that culturing may be conducted even when the culturing temperature increases to high temperature under outdoor conditions where temperature control is difficult, such as on days with abundant sunshine, for example.

MODE FOR CARRYING OUT THE INVENTION

1. Novel Strain of the Invention

Figure 1:
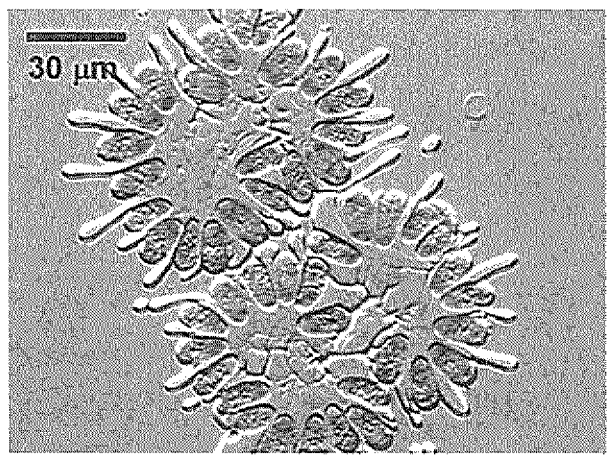
FIG. 1 is a photomicrograph of compressed cells of the strain *Botryococcus braunii* tsukuba-1.

The novel strain of *Botryococcus braunii* race-B according to the invention has the following characteristics.
External Features:

The colonies as seen by the naked eye are spherical and yellow-green to green. Compression under the microscope reveals aciniform colonies (FIG. 1). The colony sizes are an average of 30 to 100 μm, with a maximum of 500 μm.

Figure 2:
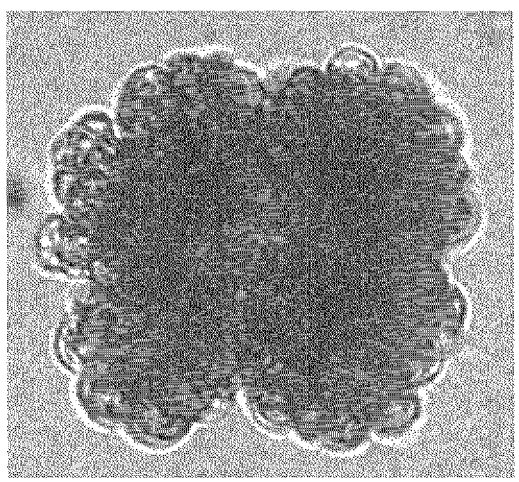
FIG. 2 is a photomicrograph of cells of the strain *Botryococcus braunii* tsukuba-1.

Cell Morphology:

Morphology: Normally clavate with cell walls, but also forming outer shells known as "socket walls", surrounding the cell walls (FIG. 2). The hydrocarbons secreted from the cells can accumulate between the cells and the outer shells.

Size: Approximately 8 μm short diameter, approximately 14 μm long diameter, ratio: approximately 1.8.

The *Botryococcus braunii* tsukuba-1 strain of the invention has been deposited in Japan at the International Patent Organism Depositary (IPOD) of the National Institute of Advanced Industrial Science and Technology (Tsukuba Central 6, 1-1, Higashi 1-chome, Tsukuba-shi, Ibaraki Prefecture, Japan 305-8566) on Dec. 9, 2010, as deposit number FERM P-22046. It was then transferred to an international depositary of the same institute under the Budapest Treaty on Nov. 25, 2011, and assigned the deposit number FERM ABP-11441.

The microorganism used for the method for producing hydrocarbons at high purity according to the invention is not limited to the strain *Botryococcus braunii* tsukuba-1, and any strain that has essentially the same microbial properties as the aforementioned strain of *Botryococcus braunii* race-B may be used.

2. Isolation of *Botryococcus* Algae

The novel strain of *Botryococcus braunii* race-B according to the invention can be isolated from a sample containing *Botryococcus* algae, harvested from lakes and ponds, using the following method.

The sample containing *Botryococcus* algae can be harvested from lakes and ponds using a plankton net with a mesh size of 30 to 100 μm.

Available chlorine is allowed to act on the sample containing the *Botryococcus* algae to sterilize the microorganisms other than *Botryococcus*. In this case, the treated sample may be pre-cultured in an appropriate medium to grow the algae. The medium may be CHU medium, JM medium, MDM medium, AF-6 medium or the like, with no particular restrictions so long as it is an appropriate medium for *Botryococcus* algae. Before using the available chlorine, the *Botryococcus* colonies may be separated by means such as centrifugal separation, filtration or a micropipette under a microscope.

After treatment of the sample with available chlorine as described above, the sample may be used directly in that form, but preferably the cells are separated by filtration or centrifugal separation and suspended in the culture solution, and this procedure is repeated for washing.

Next, the sample treated with the available chlorine is spread onto medium suitable for culturing of *Botryococcus* algae, for example, plate medium such as CHU medium, JM medium, MDM medium or AF-6 medium, and cultured. The pH of the medium may be pH 1-14, preferably pH 2-13, more preferably pH 3-11 and even more preferably pH 4-10. The culturing temperature may be in the range of usually 0° C. to 50° C., preferably 5° C. to 40° C. and more preferably 10° C. to 30° C. The culturing is conducted under photoirradiation using a fluorescent lamp. The photoirradiation may be carried out continuously, or by periodic irradiation at intervals. The time interval may be selected between 1 to 72 hours, preferably 1 to 24 hours and more preferably 1 to 12 hours. The illuminance will usually be 0-300 µE/m$^2$/s, and is preferably 5-100 µE/m/s. The culturing time will usually be 1 to 60 days, and is preferably 1 to 30 days.

Next, a single colony of the *Botryococcus* algae formed on the plate medium is harvested to obtain a single strain of *Botryococcus* algae. Harvesting of the single colony may be performed under a microscope.

The strain separated in this manner is then cultured on liquid medium. The type of liquid medium may be, for example, CHU medium, JM medium, MDM medium, AF-6 medium, or a modified form of such media. The pH of the medium may be pH 1-14, preferably pH 2-13, more preferably pH 3-11 and even more preferably pH 4-10. The culturing temperature may be in the range of usually 0° C. to 60° C., preferably 5° C. to 50° C. and more preferably 10° C. to 40° C. The culturing is conducted under photoirradiation using a fluorescent lamp. The photoirradiation may be carried out continuously, or by periodic irradiation at intervals. The time interval may be selected between 1 to 72 hours, preferably 1 to 24 hours and more preferably 1 to 12 hours. The illuminance will usually be 0-300 µE/m/s, and is preferably 5-100 µE/m/s. The culturing period will usually be 1 to 5 months, and is preferably 1 to 3 months. The culturing may be conducted with aeration or by static culturing without aeration, but it is preferably conducted by static culturing without aeration.

3. Study of Optimum Culturing Conditions

By varying the temperature during culturing on the liquid medium and measuring the amount of chlorophyll, it is possible to determine the optimum growth temperature. In this case, culturing is conducted, for example, in a 48-well microplate and the amount of chlorophyll may be measured with a microplate reader.

4. Extraction and Analysis of Hydrocarbons Produced by *Botryococcus* Algae

The hydrocarbons produced by *Botryococcus* algae can be extracted and analyzed by methods known to those skilled in the art. For example, the wet algal mass obtained by culturing and growing the *Botryococcus* algae, and recovering it from the obtained culture solution by filtration or the like, is dried by freeze-drying or heated drying. An organic solvent may then be used to extract the hydrocarbons from the algal mass mixture. The extraction may be conducted two or more times using different organic solvents. The organic solvent used may be n-hexane or a chloroform:methanol mixture (for example, 1:1 or 1:2). Preferably, extraction is performed with a chloroform:methanol mixture, and the extract is then concentrated to dryness under a nitrogen stream, and again extracted with n-hexane. The obtained extract is analyzed by NMR, IR, gas chromatography, GC/MS or the like.

The hydrocarbons produced by the *Botryococcus* strain obtained by this procedure are analyzed by the procedure described above, and a strain of *Botryococcus braunii* race-B according to the invention is obtained by screening of *Botryococcus* strains that produce at least 80% hydrocarbons of the molecular formula $C_{34}H_{58}$ (molecular weight: 466) with respect to the total hydrocarbons.

Also, *Botryococcus* strains with an optimal culturing temperature of 30° C. or higher are screened to obtain a strain of *Botryococcus braunii* race-B according to the invention.

The culturing temperature referred to here is the temperature of the liquid medium during liquid culturing. The optimal culturing temperature is the culturing temperature at the specific growth rate, when the specific growth rate is plotted against culturing temperature. The "specific growth rate" is defined as the increase in cell mass per unit time, and it can be determined by the following formula.

Specific Growth Rate $(\mu)=\ln(N_2/N_1)/(t_2-t_1)$

Here, $N_2$ and $N_1$ are the biomass at times $t_2$ and $t_1$, respectively.

5. Hydrocarbons

The hydrocarbons obtained from the strain of *Botryococcus braunii* race-B according to the invention have the following characteristics.

The produced hydrocarbons may be at 20 to 70% of cell dry weight, preferably 25 to 65% of cell dry weight, more preferably 30 to 60% of cell dry weight and even more preferably 30 to 50% of cell dry weight.

Of the total produced hydrocarbons, the proportion of hydrocarbons with the highest content is 60% of cell dry weight or greater, preferably 70% of cell dry weight or greater, more preferably 80% of cell dry weight or greater, even more preferably 90% of cell dry weight or greater, yet more preferably 95% of cell dry weight or greater and most preferably 100% of cell dry weight.

The hydrocarbons other than the hydrocarbons with the highest content may include their isomers, such as geometric isomers.

The hydrocarbons with the highest content are hydrocarbons of the molecular formula $C_{34}H_{58}$ (molecular weight: 466). These hydrocarbons may have double bonds at any positions, or they may be cyclohexenes. Preferably, the hydrocarbons have the structural formula represented by the following formula (I).

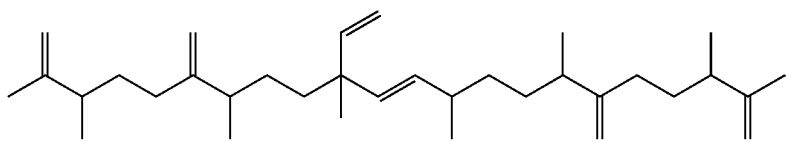

formula (I)

6. Utilization of Hydrocarbons Obtained According to the Invention

The hydrocarbons obtained according to the invention may be used directly as fuel. When used as fuel for an internal combustion engine, it is necessary to carry out thermal decomposition or cracking using a catalyst. As an example, there is known a process for producing aromatic hydrocarbons by cyclization by catalyst cracking (Banerjee A., et al., Critical Reviews in Biotechnology (CRC Press), 22). There is also known a method of selectively oxidizing the terminal vinyl groups of the obtained hydrocarbons, for utilization as a methyl ketone derivative ($C_{34}H_{56}O$) (Chisti, Y. J. Ramasay Society, 27-28, 24-26, 1980). The obtained hydrocarbons may also be polymerized by cationic polymerization, radical polymerization or ultraviolet rays, for utilization as a polymer material.

Examples of analyzing hydrocarbons separated and produced by a strain of *Botryococcus braunii* race-B according to the invention will now be described, with the understanding that the scope of the claims of the invention are not restricted by these examples.

EXAMPLE 1

1. Culturing and Isolation

A sample containing *Botryococcus* strains was harvested from lakes and ponds of various locations in Japan, using a plankton net with a mesh size of 30 to 100 μm. The *Botryococcus* colonies were isolated from the sample using a micropipette under a microscope, and after sterilizing the non-*Botryococcus* microorganisms by immersion in AF-6 medium containing available chlorine added to a concentration of about 0.1%, washing was performed 3 times with AF-6 medium (Table 1), and culturing was carried out at 22° C. under photoirradiation every 12 hours. Next, a strain cultured in 200 ml of modified Chu medium (Table 2) was added to an Erlenmeyer flask, and culturing was carried out for 1 to 3 months at 25° C., under photoirradiation every 12 hours.

TABLE 1

| Composition of modified AF-6 medium | |
|---|---|
| $NaNO_3$ | 140 mg/L |
| $NH_4NO_3$ | 22 mg/L |
| $MgSO_4 \cdot 7H_2O$ | 30 mg/L |
| $KH_2PO_4$ | 10 mg/L |
| $K_2HPO_4$ | 5 mg/L |
| $CaCl_2 \cdot 2H_2O$ | 10 mg/L |
| Citric acid | 2 mg/L |
| Iron citrate | 2 mg/L |
| Biotin | 2 g/L |
| Thiamine HCl | 10 g/L |
| Vitamin B6 | 1 g/L |
| Vitamin B12 | 1 g/L |
| P IV metals* | 5 ml/L |
| pH 8.0-8.4 | |

| *P IV metals | |
|---|---|
| $FeCl_3 \cdot 6H_2O$ | 19.6 mg |
| $MnCl_2 \cdot 4H_2O$ | 3.6 mg |
| $ZnSO_4 \cdot 7H_2O$ | 2.2 mg |
| $CoCl_2 \cdot 6H_2O$ | 0.4 mg |
| $Na_2MoO_4 \cdot 2H_2O$ | 0.25 mg |
| $Na_2EDTA \cdot 2H_2O$ | 100 mg |
| Distilled water | 100 ml |

TABLE 2

| Composition of modified Chu medium | |
|---|---|
| $KNO_3$ | 0.2 g/l |
| $K_2HPO_4$ | 0.04 g/l |
| $MgSO_4 \cdot 7H_2O$ | 0.1 g/l |
| $CaCl_2 \cdot 2H_2O$ | 0.054 g/l |
| Fe EDTA | 7 μg/l |
| $H_3BO_4$ | 28.6 μg/l |
| $MnCl_2 \cdot 4H_2O$ | 18.1 μg/l |
| $ZnSO_4 \cdot 7H_2O$ | 2.22 μg/l |
| $Na_2MoO_4 \cdot 2H_2O$ | 0.5 μg/l |
| $CuSO_4 \cdot 5H_2O$ | 0.78 μg/l |
| $CoCl_2 \cdot 6H_2O$ | 0.8 μg/l |

2. Analysis of Hydrocarbons

The obtained *Botryococcus* culture was concentrated with a 5 μm-pore filter and freeze-dried, chloroform/methanol (2:1, V/V) was used to extract the total lipids, and after concentration to dryness, extraction was again performed with n-hexane. The sample was analyzed by GC/MS according to the following procedure.

Analysis conditions: The GC (gas chromatography) conditions were as follows. Column length: 30 m, inner diameter: 0.25φmm, Df: 0.25 μm, column: DB-5 MS, split ratio: splitless, carrier gas: He, flow rate: 1.0 ml/min, injection temperature: 280° C., column temperature: 60° C. (2 min)→280° C. (5° C./min, maintained for 5 minutes). The separator temperature was 280° C. The MS (mass analysis) conditions were as follows. Model: Mstation MS-700KII, ion sources (EI and CI, positive for CI, gas: isobutene), ionization current: 200 microA, ion source vacuum: $4 \times 10^{-4}$ Pa, ionization energy: 38 eV, analysis tube vacuum: $1.0 \times 10^{-5}$ Pa, acceleration voltage: 8.0 kV, chamber temperature: 200° C., ion Mult.1.0 kV, magnetic field: HS. The exact m/z was measured by high-resolution GC/EI-MS.

3. Measurement of Optimal Culturing Temperature

The obtained *Botryococcus* strain was inoculated into a 48-well microplate containing previously added modified Chu medium, culturing was carried out at 10° C. to 40° C. in a culture chamber, and the chlorophyll increase rate was measured using a microplate reader.

4. Results

Figure 3:
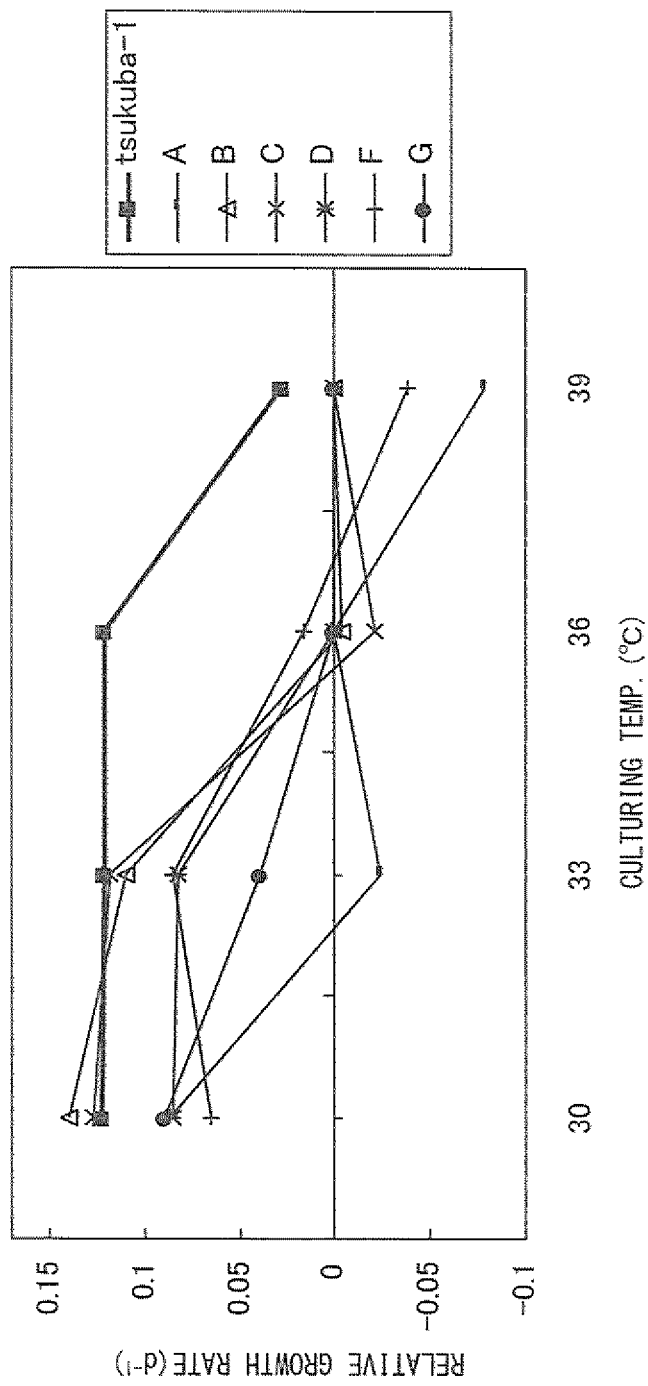
FIG. 3 is a graph showing culturing temperatures for the strain of *Botryococcus braunii* race-B according to the invention, and various algae (A-G) belonging to the genus *Botryococcus*.

Upon examining the hydrocarbon constituent components and optimal culturing temperatures for numerous other strains, it was determined that a strain obtained from the Okinawa Kanna Dam produces a hydrocarbon with a single molecular weight (92% of the simple substance, 8% geometric isomers), and is capable of growth near 35° C. in which other strains do not grow (FIG. 3).

This strain was deposited as *Botryococcus braunii* tsukuba-1 at the International Patent Organism Depositary (IPOD) of the National Institute of Advanced Industrial Science and Technology (Tsukuba Central 6, 1-1, Higashi 1-chome, Tsukuba-shi, Ibaraki Prefecture, Japan 305-8566), as deposit number FERM P-22046. It was then transferred to an international depository of the same institute under the Budapest Treaty on Nov. 25, 2011, and assigned the deposit number FERM ABP-11441.

The features of the *Botryococcus braunii* tsukuba-1 strain are as follows.

Figure 4:
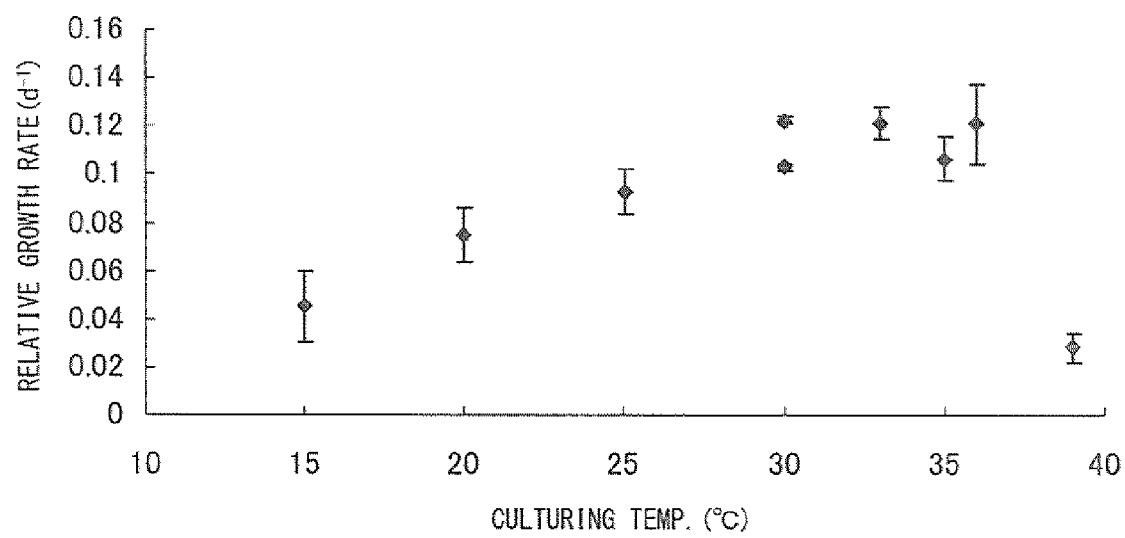
FIG. 4 is a graph showing specific growth rates at culturing temperatures for the strain of *Botryococcus braunii* race-B according to the invention.

- The optimal culturing temperature is 30° C. to 36° C., and culturing can be conducted at 15° C. to 40° C. (FIG. 4).
- Culturing can be conducted in a wide pH range of pH 4-10.
- It easily adheres to stainless steel and ceramics.
- The cells are clavate, with average lengths of about 14 μm and average widths of about 7.6 μm, the ratio being approximately 1.8.
- The colonies are yellow-green to green, with the tips of the clavate cells protruding from the colonies, and the sizes are usually 30 to 100 μm, reaching a maximum of 500 μm.
- The produced hydrocarbons are secreted extracellularly, and accumulate between the cells and the outer shells called socket walls which surround the cells, being retained within the colonies.
- The hydrocarbons accumulated within the colonies easily exude out when a glass cover is placed thereover.
- A granular structure containing numerous hydrocarbons is also observed inside the cells.

Focusing on culturing temperature, since most algae of the genus *Botryococcus* do not grow at 35° C. and higher, the *Botryococcus braunii* tsukuba-1 strain of the invention alone can be selectively obtained by culturing at 35° C. or higher.

The structure of the hydrocarbon produced by the *Botryococcus braunii* tsukuba-1 strain was confirmed by GC/MS, $^1$H and $^{13}$C-NMR, and it was determined to be a hydrocarbon with the structure represented by formula (I) below, having 5 vinyl groups in the molecule. Table 3 shows the results of GS/MS measurement.

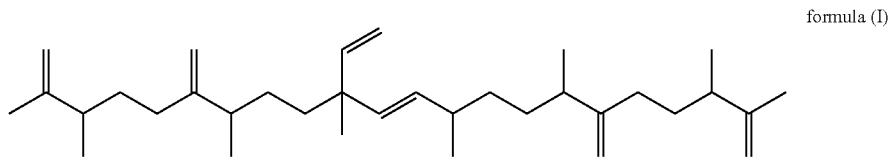 [SMILES: C=CC(C)(/C=C/C(C)CCC(C)C(=C)CCC(C)C(=C)C)CCC(C)C(=C)CCC(C)C(=C)C]

formula (I)

TABLE 3

| GS/MS measurement results | |
|---|---|
| Measuring apparatus | |
| GC/EI-MS | m/z 466 (M+) |
| GC/CI-MS | m/z 467 (M + H)+ |
| High-resolution GC/EI-MS | exact m/z 466. 45380 (−0.8 mmu) |

[Deposit Number]

*Botryococcus* tsukuba 1 FERM ABP-11441

What is claimed is:

1. A method for producing a hydrocarbon from a strain belonging to *Botryococcus braunii* race-B that produces a hydrocarbon of the molecular formula $C_{34}H_{58}$ at 60% by weight or greater with respect to the total produced hydrocarbons, comprising the steps of culturing said strain at a temperature of 35° C. to 50° C., and then extracting said hydrocarbon from said cultured strain with at least one organic solvent, wherein said strain is *Botryococcus braunii* tsukuba-1 (deposit number: FERM ABP-11441).

2. The method according to claim 1, wherein the culturing is conducted at a temperature of 39° C.

3. The method according to claim 1, wherein the culturing is conducted at a temperature of 36° C.

4. The method according to claim 1, wherein the hydrocarbon of the molecular formula $C_{34}H_{58}$ has the structure of the following Formula (I):

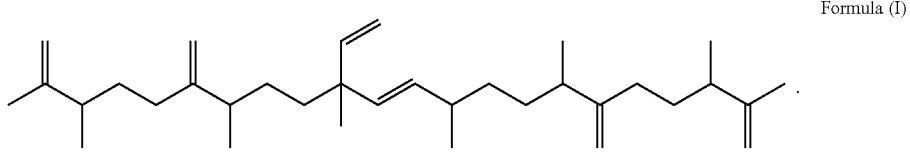 [SMILES: C=CC(C)(/C=C/C(C)CCC(C)C(=C)CCC(C)C(=C)C)CCC(C)C(=C)CCC(C)C(=C)C]

Formula (I)

5. The method of claim 1, wherein the culturing is conducted at a temperature of 35° C. to 40° C.

6. The method of claim 5, wherein the culturing is conducted at a temperature of 35° C. to 36° C.

7. The method of claim 1, wherein the at least one organic solvent is n-hexane.

8. The method of claim 1, wherein the at least one organic solvent is a mixture of chloroform and methanol.

9. The method of claim 8, wherein the at least one organic solvent is a 1:1 mixture of chloroform and methanol.

10. The method of claim 8, wherein the at least one organic solvent is a 1:2 mixture of chloroform and methanol.

11. The method of claim 8, wherein the hydrocarbon extracted is concentrated to dryness under a nitrogen stream and again extracted with n-hexane.

12. The method of claim 1, wherein the culturing is conducted for a period of 1 to 5 months.

13. The method of claim 12, wherein the culturing is conducted for a period of 1 to 3 months.

* * * * *